US012805786B2

(12) United States Patent
Nikula et al.

(10) Patent No.: US 12,805,786 B2
(45) Date of Patent: Nov. 24, 2026

(54) BIO-SIGNAL RECEIVING DEVICE, FLEXIBLE PATCH ELECTRODE STRUCTURE, BIO-SIGNAL APPARATUS AND CONNECTION METHOD OF BIO-SIGNAL APPARATUS

(71) Applicant: BITTIUM BIOSIGNALS OY, Kuopio (FI)

(72) Inventors: Arto Nikula, Kuopio (FI); Juha Myllykangas, Kuopio (FI)

(73) Assignee: BITTIUM BIOSIGNALS OY, Kuopio (FI)

( * ) Notice: Subject to any disclaimer, the term of this patent is extended or adjusted under 35 U.S.C. 154(b) by 459 days.

(21) Appl. No.: 18/474,742

(22) Filed: Sep. 26, 2023

(65) Prior Publication Data

US 2025/0099006 A1 Mar. 27, 2025

(51) Int. Cl.

*A61B 5/00* (2006.01)
*A61B 5/273* (2021.01)

(52) U.S. Cl.

CPC ............ *A61B 5/273* (2021.01); *A61B 5/6833* (2013.01); *A61B 2562/164* (2013.01); *A61B 2562/227* (2013.01)

(58) Field of Classification Search

CPC ......... A61B 5/282; A61B 5/0006; A61B 5/28; A61B 5/6833; A61B 2560/0412;

(Continued)

(56) References Cited

U.S. PATENT DOCUMENTS 4,490,005 A 12/1984 Hovey
5,234,355 A * 8/1993 Sosinski ............ H01R 13/4364 439/337

(Continued)

OTHER PUBLICATIONS

Feb. 20, 2025 Search Report issued in European Patent Application No. 24201978.4, pp. 1-14.

*Primary Examiner* — Joseph A Stoklosa
*Assistant Examiner* — Brian M Antiskay
(74) *Attorney, Agent, or Firm* — Nixon & Vanderhye PC

(57) ABSTRACT

A first mechanical connection part associated with a bio-signal receiving device is connected with a second mechanical connection part of a flexible patch electrode structure. An asymmetrical plate structure of a first mechanical connection part is inserted through a correspondingly asymmetrical hole of the second mechanical connection part of a flexible patch electrode structure. The asymmetrical plate structure is integrated with a bar and another side of the bar being coupled with a plane arrangement of the first mechanical connection part. The asymmetrical plate structure and the plane arrangement having a non-zero distance therebetween. Connection and orientation between the first mechanical connector and the second connection part is limited to those with acceptance of the asymmetry. The bio-signal receiving device and the flexible patch electrode structure are rotated with respect to each other round a rotational axis that is parallel to a longitudinal axis of the at least one bar in order to move an upper surface of the asymmetrical plate structure against the flat structure, the lower surface facing the plane arrangement, and the rotation causing a mechanical and electrical connection between the bio-signal receiving device and the flexible patch electrode structure.

12 Claims, 4 Drawing Sheets

(58) Field of Classification Search

CPC ....... A61B 5/25; A61B 5/02438; A61B 5/308; A61B 5/332; A61B 5/6831; A61B 5/1118; A61B 5/287; A61B 5/681; A61B 2560/0468; A61B 5/6804; A61B 5/369; A61B 2562/227; A61B 5/6824; A61B 5/256; H01R 4/54; H01R 13/10; H01R 13/213; H01R 13/625; H01R 33/46; H01R 33/9456

USPC .......................... 600/372, 382–395, 508–509

See application file for complete search history.

(56) References Cited

U.S. PATENT DOCUMENTS

| | | | | | |
|---|---|---|---|---|---|
| 7,866,992 | B2 * | 1/2011 | Pfeiffer | H01R 13/625 | 439/140 |
| 9,775,561 | B2 * | 10/2017 | Russell | A61B 5/256 | |
| 10,107,482 | B1 * | 10/2018 | Hill | H01R 13/213 | |
| 11,944,441 | B2 * | 4/2024 | Pernu | A61B 5/6823 | |
| 2013/0183854 | A1 * | 7/2013 | Huang | H01R 35/04 | 439/534 |
| 2014/0128710 | A1 * | 5/2014 | Nakamura | H01M 50/216 | 429/100 |
| 2014/0336493 | A1 * | 11/2014 | Kulach | A61B 5/6831 | 600/390 |
| 2014/0349527 | A1 * | 11/2014 | Himeno | H01R 4/32 | 439/754 |
| 2015/0164422 | A1 * | 6/2015 | Lee | A61B 5/6831 | 600/300 |
| 2018/0175564 | A1 * | 6/2018 | Komoto | H01R 24/005 | |
| 2018/0271414 | A1 | 9/2018 | Deck et al. | | |
| 2020/0268250 | A1 | 8/2020 | Yomtov | | |
| 2021/0128042 | A1 * | 5/2021 | Herberger | A61B 5/6833 | |
| 2021/0338128 | A1 * | 11/2021 | Le Lous | A61B 5/256 | |
| 2023/0248290 | A1 | 8/2023 | Myllykangas et al. | | |

* cited by examiner

BIO-SIGNAL RECEIVING DEVICE, FLEXIBLE PATCH ELECTRODE STRUCTURE, BIO-SIGNAL APPARATUS AND CONNECTION METHOD OF BIO-SIGNAL APPARATUS

FIELD

The invention relates to a bio-signal receiving device, a flexible patch electrode structure, bio-signal apparatus and a connection method of a bio-signal apparatus.

BACKGROUND

An electronic device, which measures bio-signals such as ECG (ElectroCardioGram) and EEG (ElectroEncephalo-Gram), must be well contacted with the electrodes that are in contact with the body and mechanically reliably fixed to its support. At least some kind electromechanical part is used for connecting and attaching a non-disposable bio-signal measurement device with a disposable patch electrode arrangement, and the electromechanical part is structurally and/or electrically rather complicated. It may also contain metal parts or even some assembled electrical connector to interface with the non-disposable bio-signal measurement device. There has been development in this field but further improvement is still desired.

BRIEF DESCRIPTION

The present invention seeks to provide an improvement in the measurements.

The invention is defined by the independent claims. Embodiments are defined in the dependent claims.

If one or more of the embodiments is considered not to fall under the scope of the independent claims, such an embodiment is or such embodiments are still useful for understanding features of the invention.

LIST OF DRAWINGS

Example embodiments of the present invention are described below, by way of example only, with reference to the accompanying drawings, in which FIGS. 1 to 3 illustrate examples of connection structures of a bio-signal apparatus;

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment.

The articles "a" and "an" give a general sense of entities, structures, components, compositions, operations, functions, connections or the like in this document. Note also that singular terms may include pluralities.

Single features of different embodiments may also be combined to provide other embodiments. Furthermore, words "comprising" and "including" should be understood as not limiting the described embodiments to consist of only those features that have been mentioned and such embodiments may also contain features/structures that have not been specifically mentioned. All combinations of the embodiments are considered possible if their combination does not lead to structural or logical contradiction.

Many bio-signals are electrical signals formed by the nervous system or electrical conduction system of a mammal and hence such signals may also be in such cases called bioelectrical signals. Some other bio-signals are not electrical signals, per se, and examples of such signals are temperature and sound.

Patch electrode structure 18 comprises a second electrical connector structure 104, which is electrically connected with the electrodes 50 through electrical conductors of the patch electrode structure 18. The electrical conductors of the patch electrode structure 18 are not shown in Figs because a person skilled in the art is familiar with a patch electrode structure, per se.

The patch electrode structure 18 is typically a piece of sheet that may be narrow like a band or broad like a wide planar surface and it is often fairly thin and flexible. Thickness of the patch electrode structure 18 may resemble those of sheet of plastic, paper, board or cloth. The patch electrode structure 18 is configured to be in contact with skin or mucous membrane of a mammal such as a human being for a bio-signal measurement. The bio-signal may be related to body movement, body temperature, heart rate variability, electrocardiogram, electromyogram, electroencephalogram or the like for example. During a measurement, the patch electrode structure 18 feeds directly or indirectly electrical bio-signals to a non-disposable bio-signal receiving device 200 that is separate from the patch electrode structure 18. The disposable patch electrode structure 18 may have a PET-layer, for example.

Figure 1:
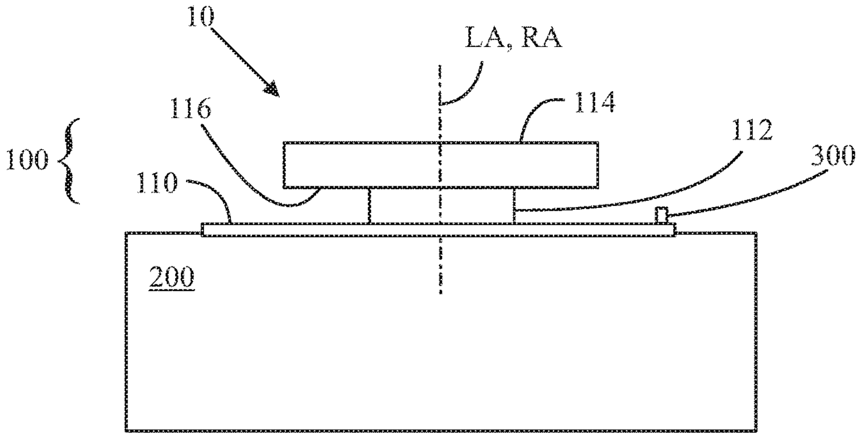
Figure 2:
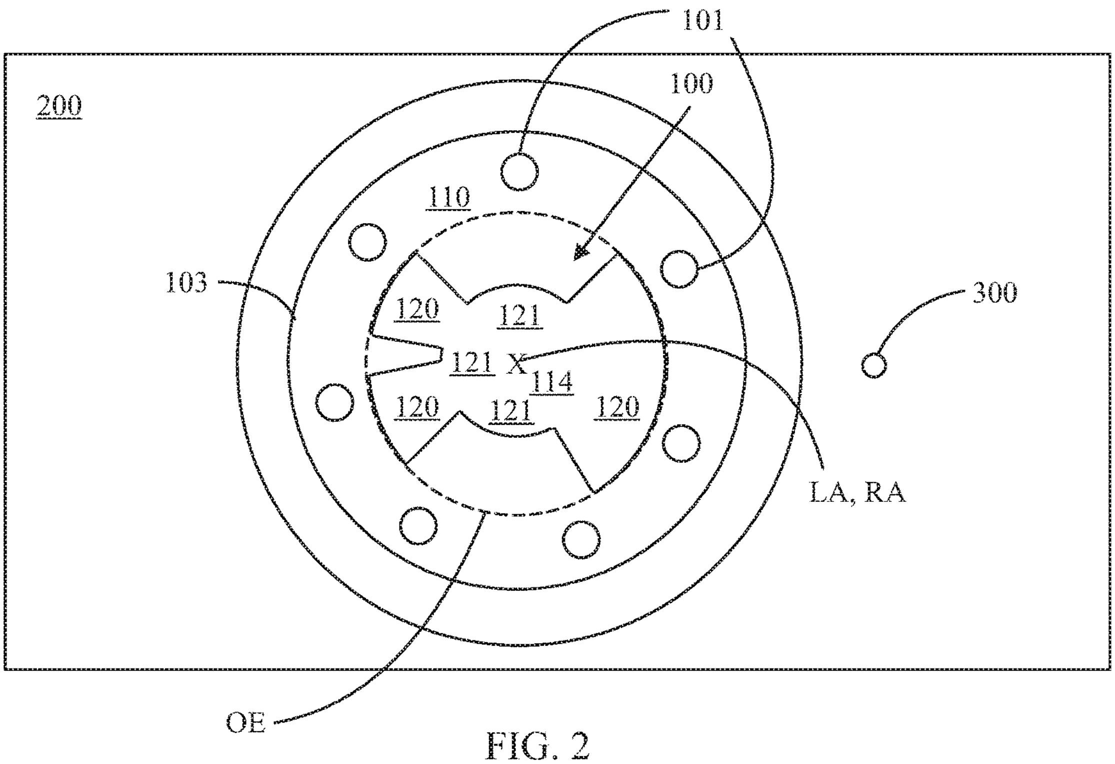
Figure 3:
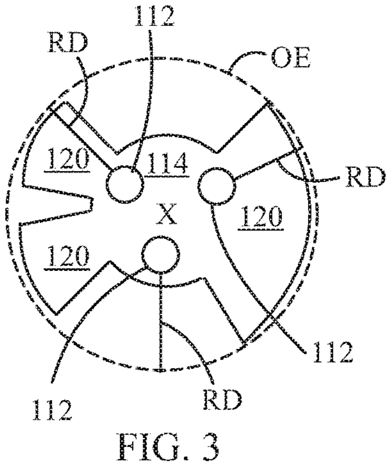

FIGS. 1, 2 and 3 illustrate examples of connection structures of a bio-signal apparatus. A bio-signal receiving device 200 is both mechanically and electrically coupled with the first connection part 10 that comprises a first mechanical connector 100 and a first electrical connector structure 103 for an external connection. The coupling between the bio-signal receiving device 200 and the first connection part 10 may be fixed so effectively that the first connection part 10 may also be considered a structural part of the bio-signal receiving device 200. Still, the first connection part 10 may be detached from the bio-signal receiving device 200 or the rest of the bio-signal receiving device 200 by one or more tools.

The first connection part 10 comprises a plane arrangement 110 that comprises the first electrical connector structure 103 on an outer surface of the plane arrangement 110. The first electrical connector structure 103 comprises electrical connectors 101 such as electrical pads for an electrical coupling. The electrical connectors 101 are electrically coupled with an electrical circuit of the bio-signal receiving device 200. The coupling may be based on electrical conductors therebetween.

The first mechanical connector 100 comprises at least one bar 112 and an asymmetrical plate structure 114. A longitudinal axis LA of the bar 112 is at least approximately parallel to a normal to the plane arrangement 110. The longitudinal axis LA of the at least one bar 112 is also parallel to a rotational axis RA. The at least one bar 112 is integrated with the asymmetrical plate structure 114. One end of each of the at least one bar 112 is in contact with the asymmetrical plate structure 114. The integration may mean that the asymmetrical plate structure 114 and the at least one bar 112 are of the same material in a continuous manner. The integration may mean that the asymmetrical plate structure 114 and the at least one bar 112 are separate pieces of material but they are attached with each other. Another end of the at least one bar 112 is structurally coupled with the plane arrangement 110. The at least one bar 112 may be structurally attached with the plane arrangement 110.

The plane arrangement 110 and the at least one bar 112 may be of the same material in a continuous manner. The plane arrangement 110 and the at least one bar 112 may be separate pieces of material attached with each other. The asymmetrical plate structure 114 and the plane arrangement 110 have a non-zero distance therebetween based on a height of the at least one bar 112. As shown in FIG. 3, each of the at least one bar 112 and the outer envelope OE of the asymmetrical plate structure 114 have a non-zero radial distance RD with each other.

The asymmetrical plate structure 114 limits a connection and orientation between the first mechanical connector 100 and a counterpart to those with acceptance of the asymmetry. That is, both the plate 114 and its counterpart must be compatible with each other from the asymmetry point of view.

The asymmetrical plate structure 114 is inserted into a counterpart and the first mechanical connection part 100 is connected with the counterpart by a rotation between them. The rotation moves an upper surface 116 of the asymmetrical plate structure 114 against a surface of the counterpart, the upper surface 116 facing the plane arrangement 110. The counterpart structure enters to a gap between the upper surface 116 and the plane arrangement 110, which mechanically couples the asymmetrical plate structure 114 and the counterpart together. A backward rotation enables disconnection between the asymmetrical plate structure and the counterpart. A possible counterpart is the second connection part 12 of the flexible patch structure 18, which enables a connection and a disconnection between the bio-signal receiving device 200 and the flexible patch structure 18.

In an embodiment, the asymmetrical plate structure 114 extends radially in all directions from a rotational axis RA such that some sectors extend further than some other sectors. Thus, the asymmetrical plate structure 114 comprises several sectorial extensions 120 that extend radially further outward from the rotational axis RA than neighboring sectorial sections 121 of the asymmetrical plate structure 114 beside them as shown in FIG. 2. A middle area 20 round the rotational axis RA in all sectors is not a part of the sectorial extensions 120. The middle area is a circle with a radius a length of which is the same as a distance between an outer borderline of any one of the sectorial sections 121 and the rotational axis RA. At least two of the sectoral extensions 120 have a different extension length from the rotation axis RA compared to the sectorial sections 121. Each of the at least one bar 114 can be considered to locate in the middle area.

In an embodiment, at least part of the first connection part 10 is made of a wear-proof and/or abrasion-resistant material that is resistant to wear and friction caused by repeated attachment and release with a counterpart. The material of the first connection part 10 may be tougher than that of a case of the bio-signal receiving device 200. In an embodiment, the asymmetrical plate structure 114 is made of wear-proof and/or abrasion-resistant material while the bar 112 and the plane arrangement 110 are not necessarily made of such material or material of corresponding wear-proof and/or abrasion-resistance.

Figure 4:
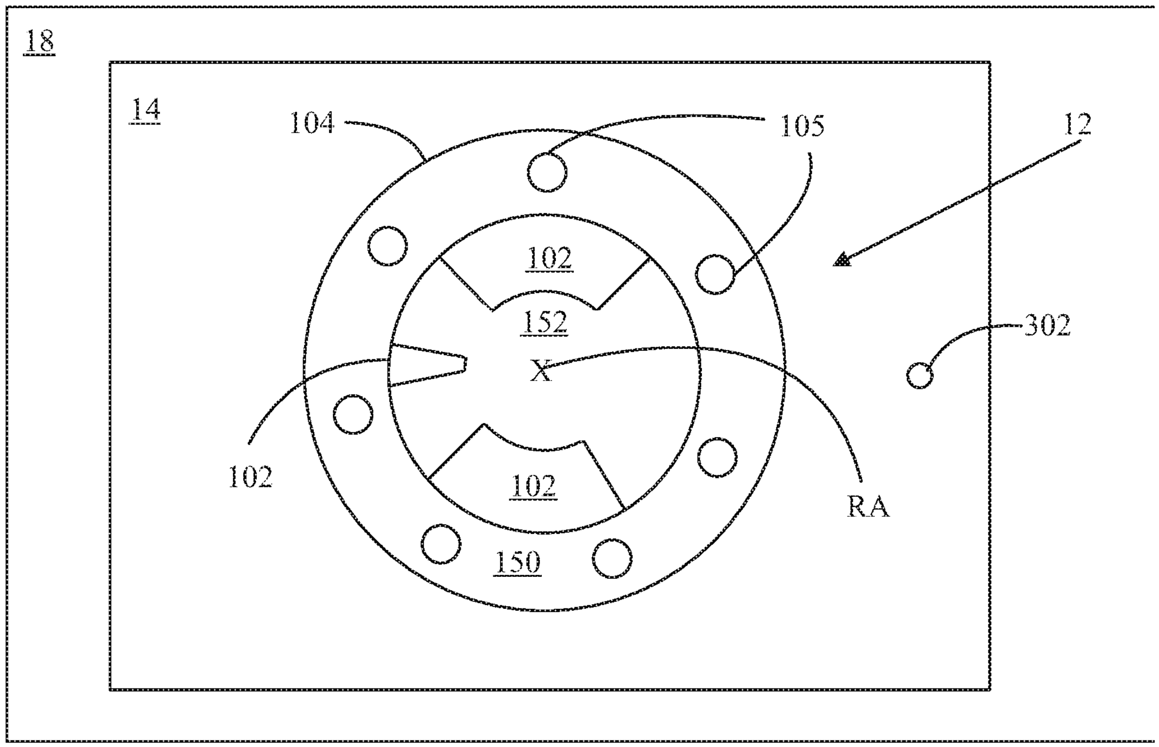
FIG. 4 illustrates examples of connection structures of a flexible electrode structure.
Figure 5:
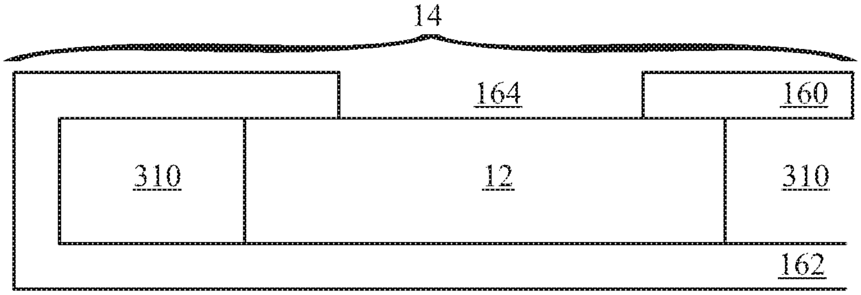
FIG. 5 illustrates an example of a fold area of a flexible patch electrode structure.
Figure 7:
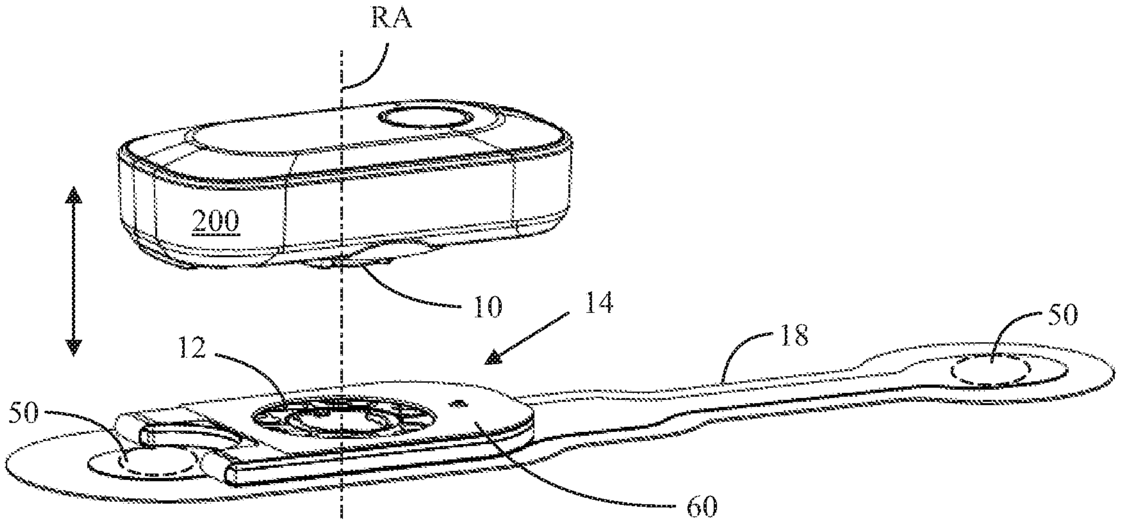
FIG. 7 illustrates an example of both the bio-signal receiving device and the flexible patch electrode structure in a position before their connection to or after their release from each other.

A flexible patch electrode structure 18 of a bio-signal apparatus comprises skin electrodes 50 for contact with the skin of a mammal as shown in an example of FIG. 7. FIG. 4 illustrates an example where a second connection part 12 of the flexible patch electrode structure 18 is at least partially located within a fold 14 of the flexible patch electrode structure 18. Example of FIG. 5 illustrates that the flexible patch electrode structure 18 has also an opening 164 that reveals the second connection part 12 for a connection with the first connection part 10 of the bio-signal receiving device 200, for example. The opening 164 is located in one or both layers 160 and 162 of the fold 14 of the flexible patch structure 200 (FIG. 5 shows an example where the opening 164 is only in one layer).

The second electrical connection part 12 is in an electrical connection with the skin electrodes 50 through conductors of the structure of the flexible patch electrode structure 18 (this feature is not illustrated in Figs but a person skilled in the art is familiar with such connections in the flexible patch electrode structure 18, per se).

As shown in example of FIG. 4, the second connection part 12 comprises a second mechanical connector 102 and second electrical connector structure 104 for an electrical and mechanical connection with a counterpart, such as that associated with the bio-signal receiving device 200. The first connection part 10 enables a repeated attachment and release with the counterpart, and the second connection part 12 may also enable a plurality of connections and releases. The connection between the first electrical connector structure 103 and the second electrical connector structure 102 enables transfer of a bio-signal received by the skin electrodes 50 through the second connection part 12 toward the counterpart in response to the attachment.

The second connection part 12 comprises a plane structure 150 that comprises an asymmetrical hole 152 therethrough. The asymmetrical hole 152 and the asymmetrical plate structure 114 are similarly asymmetrical which enables insertion of the asymmetrical plate structure 114 into the asymmetrical hole 152. That is, the asymmetrical hole 152 is wide in locations which are configured to accept the sectorial extensions 120 and correspondingly the asymmetrical hole 152 is narrow in locations which are configured to accept the sectorial sections 121. That the asymmetrical hole 152 is wide means that a diameter of the asymmetrical hole 152 is larger in such a location than in a location where the asymmetrical hole 152 is narrow.

The second electrical connector structure 104 is on a second side of the plane structure 150. The second side is opposite to a first side, the first side facing the skin in conjunction with an application of the flexible patch electrode structure 18 to the skin. In that manner the first electrical connector structure 103 and the second electrical connector structure 104 may face each other that enables a galvanic contact between electrical connectors 101 associated with the bio-signal receiving device 200, for example, and electrical connectors 105 of the plane structure 150 of the flexible patch electrode structure 18 (see FIG. 7). Note that the plane arrangement 110 and the plane structure 150 may be flat or curved similarly in order to match together.

Figure 6:
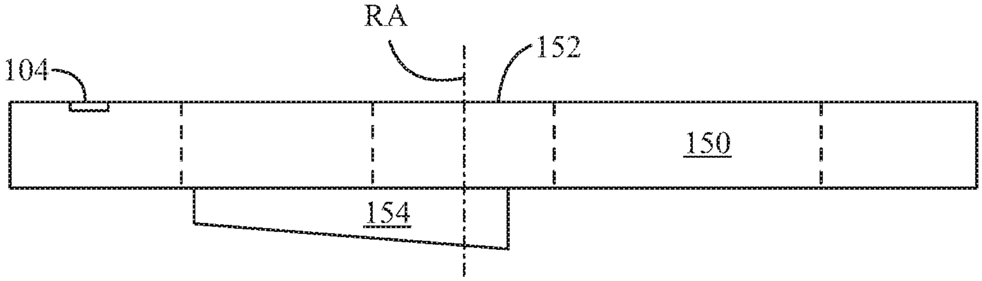
FIG. 6 illustrates an example of a wedge structure.

In an embodiment an example of which is illustrated in FIG. 6, the second connection part 12 may comprise a wedge structure 154 curved at least partially round the asymmetrical hole 152 on the opposite side to the second electrical connector structure 104.

In an embodiment, the asymmetrical hole 152 and the wedge structure 154 are parts of the second connector 12. The asymmetrical hole 152 and the counterpart that accepts the asymmetry are configured to attach together in response to a rotational movement between the second connection part 12 and the counterpart. The counterpart may be the first mechanical connection part 100 or the like for example.

The wedge structure 154 may cause tightening and loosening a mechanical connection between the second mechanical connector 12 and the counterpart in response to a rotational movement between the second connection part 12 and the counterpart.

The wedge structure 154 may thus enable tightening the connection between the first mechanical connection part 100 and the second mechanical connection part 102 in response to rotation in one direction. Correspondinly, the wedge structure 154 enables loosening the connection between the first mechanical connection part 100 and the second mechanical connection part 102 in response to rotation in an opposite direction.

In an embodiment that is illustrated in FIGS. 4 and 5, the fold 14 may comprise two layers 160, 162 of the flexible patch electrode structure 18. The layer 160 is different from a layer 162 that is for a skin contact. The layer 160 comprises the opening 164 that reveals the second connection part 12 for a connection, the second connection part 12 being between the two layers 160, 162.

The asymmetrical plate structure 114 is configured to pass through the asymmetrical hole 152 in a position allowed by a common asymmetry and proceed on the wedge structure 154 in response to a rotation between the first connection part 10 and the second connection part 12, a rotational axis being parallel with a longitudinal axis of the bar 112.

The wedge structure 154 is configured to cause tightening and loosening the mechanical connection between the first mechanical connector 100 and the second mechanical connector 102 in response to the direction of rotational movement between the first connection part 10 and the second connection part 12. The rotation is configured to move a surface 116 of the asymmetrical plate structure 114, which faces the plane arrangement 110, against a surface of the plane structure 150 of the second connection part 12. The surface of the plane structure 150 against which the asymmetrical plane structure 114 moves is on the same side as the skin electrodes.

In an embodiment, the flexible patch electrode 18 may comprise a first positional structure 300 that is a counterpart for a second positional structure 302 of the first connection part 10. The first positional structure 300 and the second positional structure 302 are configured to attach together in response to the rotation tightening the mechanical connection between the first mechanical connector 10 and the second mechanical connector 12 by the rotational movement between the first connection part 10 and the second mechanical connector 12. The first positional structure 300 and the second positional structure 302 keep the flexible patch electrode 18 and the bio-signal receiving device 200 immobile with respect to each other during their attachment together.

The folded section, which comprises an elastic structure 310 within the fold 14 that can also be called a folded section causes a spring force to attachment of the first connection part 10 and the second connection part 12 when they attached together in a normally tightened manner. The fold 14 is formed such that the patch electrode structure 18 at one end is folded over such so that a part of the electrode structure 18 is positioned on top of another part. An elastic structure 310 may be inserted between the parts positioned on each another as illustrated in FIG. 5. The elastic structure 310 may be made of plastic, for example. The elastic structure 310 may comprise soft polymer foam, which is compressible, and the soft polymer responds to force compressing it with a force of the same magnitude but of opposite direction. That is, the soft polymer provides a force as a function of compression.

A surface foam 60, which is shown in FIG. 7, may seal the connection between the bio-signal receiving device 200 and the patch electrode structure 18 and thus protect the connection from moisture and dirt. The surface foam 60 also creates pressure based on a spring force that increases friction between the surfaces such that the bio-signal receiving device 200 and the patch electrode structure 18 stay in place with respect to each other. The surface foam 60 will be new each time the patch electrode structure 18 is changed.

In an embodiment an example of which is illustrated in FIG. 1, the mechanical connector 100 may comprise at least one locking pin 300 and the patch electrode structure 18 may have a corresponding locking hole 302 for each of the at least one locking pin 300. Each of the at least one locking pin 300 is inserted in a corresponding locking hole of the at least one hole 302 for aligning and keeping the bio-signal receiving device 200 and the patch electrode structure 18 in a desired and/or suitable position with respect to each other in response to the first connection part 10 and the second connection part 12 being fastened together. The at least one locking pin 300 may extend upto the bio-signal receiving device 200 which has a corresponding locking hollow (not shown in Figs). Alternatively, the bio-signal receiving device 200 may comprise all or one or more locking pins 300. When the at least one pin 300 enters the corresponding locking hole 302, the parts of whole apparatus become immobile with respect to each other which makes the apparatus firm and easy to use and keep the apparatus in hand.

Figure 8:
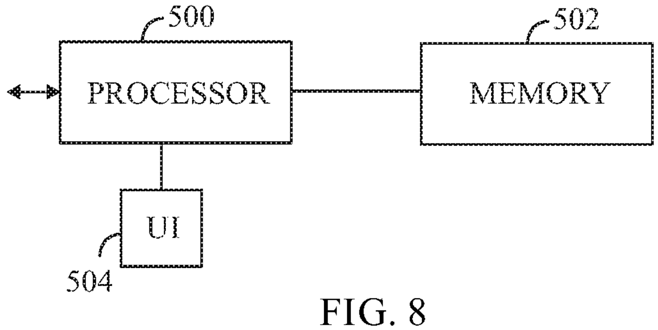
FIG. 8 illustrates an example of a data processing unit of the bio-signal apparatus.

FIG. 8 illustrates an example of the bio-signal receiving device 200 of the bio-signal apparatus. The bio-signal receiving device 200 may comprise one or more processors 500 and one or more memories 502 including computer program code. The one or more memories 502 and the computer program code may be configured to, with the one or more processors 500, cause the bio-signal apparatus at least to receive bio-signal from the patch electrode structure 18 and perform data processing of the bio-signal. Additionally, the data processing unit 500 may control the bio-signal measurement and the bio-signal receiving device 200. The bio-signal receiving device 200 may include a user interface 504.

The user interface 504 means an input/output device and/or unit. Non-limiting examples of a user interface include a touch screen, other electronic display screen, keyboard, mouse, microphone, handheld electronic controller, digital stylus, display screen, speaker, and/or projector for projecting a visual display.

The term "computer" includes a computational device that performs logical and arithmetic operations. For example, a "computer" may comprise an electronic computational device, such as an integrated circuit, a microprocessor, a mobile computing device, a laptop computer, a tablet computer, a personal computer, or a mainframe computer. A "computer" may comprise a central processing unit, an ALU (arithmetic logic unit), a memory unit, and a control unit that controls actions of other components of the computer so that steps of a computer program are executed in a desired sequence. A "computer" may also include at least one peripheral unit that may include an auxiliary memory (such as a disk drive or flash memory), and/or may include data processing circuitry.

A bio-signal apparatus comprises both the bio-signal receiving device 200 the flexible patch electrode structure 18 illustrated in FIGS. 1 to 8.

Figure 9:
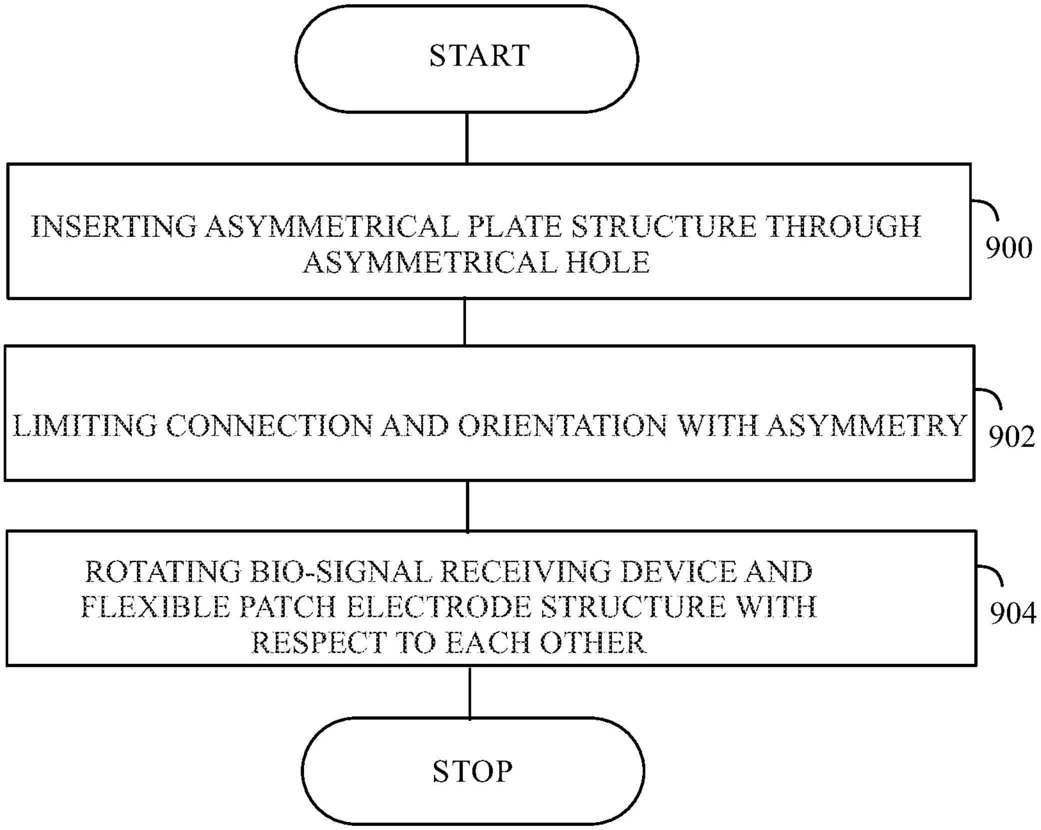
FIG. 9 illustrates of an example of a flow chart of a connection method.

FIG. 9 is a flow chart of the measurement method. A first mechanical connection part 100 associated with a bio-signal receiving device 200 is connected with a second mechanical connection part 12 of a flexible patch electrode structure 18 in the following manner.

In step 900, an asymmetrical plate structure 114 of a first mechanical connection part 100 of a bio-signal receiving device 200 is inserted through an correspondingly asymmetrical hole 152 of the second mechanical connection part 102 of a flexible patch electrode structure 18, the asymmetrical plate structure 114 being structurally integrated with one side of at least one bar 112 and another side of the at least one bar 112 being coupled with a plane arrangement 110 of the first mechanical connection part 100, the asymmetrical plate structure 114 and the plane arrangement 110 having a non-zero distance therebetween.

In step 902, connection and orientation between the first mechanical connector 100 and the second connection part 102 is limited to those with acceptance of the asymmetry.

In step 904, the bio-signal receiving device 200 and the flexible patch electrode structure 18 are rotated with respect to each other round a rotational axis RA that is parallel to a longitudinal axis LA of the at least one bar 112 in order to move an upper surface 116 of the asymmetrical plate structure 114 against the flat structure 150, the lower surface 116 facing the plane arrangement 110, the rotation causing a mechanical and electrical connection of the bio-signal receiving device 200 and the flexible patch electrode structure 18 together.

It will be obvious to a person skilled in the art that, as technology advances, the inventive concept can be implemented in various ways. The invention and its embodiments are not limited to the example embodiments described above but may vary within the scope of the claims.

What is claimed is:

1. A bio-signal receiving device of a bio-signal apparatus, wherein the bio-signal receiving device is both mechanically and electrically coupled with a first connection part that comprises a first mechanical connector and a first electrical connector structure;

wherein the first connection part comprises a plane arrangement that comprises the first electrical connector structure on an outer surface of the plane arrangement;

wherein the first mechanical connector comprises at least one bar, and an asymmetrical plate structure and the at least one bar are integrated together at one end of the at least one bar such that each of the at least one bar and an outer envelope of the asymmetrical plate structure have a non-zero radial distance with each other while another end of the at least one bar is coupled with the plane arrangement, the asymmetrical plate structure and the plane arrangement having a non-zero distance therebetween;

wherein the asymmetrical plate structure is configured to limit a connection and orientation between the first mechanical connector and a counterpart to those with acceptance of the asymmetry; and wherein the asymmetrical plate structure is configured to connect the first mechanical connection part with the counterpart by a rotation between them, the rotation being configured to move an upper surface of the asymmetrical plate structure against a surface of the counterpart, the upper surface facing the plane arrangement.

2. The bio-signal receiving device of claim 1, wherein the asymmetrical plate structure is configured to extend radially around a rotational axis and comprises several sectorial extensions.

3. The bio-signal receiving device of claim 1, wherein the first connection part is made of a wear-proof material that is resistant to wear caused by the repeated attachment and release and that is tougher than a case of the bio-signal receiving device.

4. A bio-signal apparatus, wherein the bio-signal apparatus comprises a bio-signal receiving device and at least one of a first connection part and flexible patch electrode structure;

wherein the bio-signal receiving device is both mechanically and electrically coupled with the first connection part that comprises a first mechanical connector and a first electrical connector structure;

wherein the first connection part comprises a plane arrangement that comprises the first electrical connector structure on an outer surface of the plane arrangement;

wherein the first mechanical connector comprises at least one bar and an asymmetrical plate structure and the at least one bar is integrated together at one end of the at least one bar such that each of the at least one bar and an outer envelope of the asymmetrical plate structure have a non-zero radial distance with each other while another end of the at least one bar is structurally coupled with the plane arrangement, the asymmetrical plate structure and the plane arrangement having a non-zero distance therebetween;

wherein the asymmetrical plate structure is configured to limit a connection and orientation between the first mechanical connector and a counterpart to those with acceptance of the asymmetry;

wherein the asymmetrical plate structure is configured to connect the first mechanical connection part with the counterpart by a rotation between them, the rotation being configured to move an upper surface of the asymmetrical plate structure against a surface of the counterpart, the upper surface facing the plane arrangement; and the flexible patch electrode structure comprises skin electrodes for a contact with the skin of a mammal, and a second connection part that is located within a fold of the flexible patch electrode structure, the flexible patch electrode structure having an opening that is configured to reveal the second connection part for a connection;

the second electrical connection part is in an electrical connection with the skin electrodes;

the second connection part comprises a second mechanical connector and second electrical connector structure for an electrical and mechanical connection with a counterpart for a repeated attachment and release and for transferring a bio-signal received by the skin electrodes through the second connection part toward the counterpart in response to the attachment;

the second connection part comprises a flat structure that comprises an asymmetrical hole therethrough, and the second electrical connector structure is on a second side of the flat structure that is opposite to a first side that is configured to face the skin in conjunction with an application of the flexible patch electrode structure to the skin; and the asymmetrical hole and the wedge structure are parts of the second connector, and the asymmetrical hole and the counterpart that accepts the asymmetry are configured to attach together in response to a rotational movement between the second connection part and the counterpart.

5. The bio-signal apparatus of claim 4, characterized in that the first connection part and the second connection part are configured to connect with each other;

the asymmetrical plate structure is configured to pass through the asymmetrical hole in a position allowed by a common asymmetry and proceed on the wedge structure in response to a rotation between the first connection part and the second connection part, a rotational axis being parallel with a longitudinal axis of the bar;

the wedge structure is configured to cause tightening and loosening the mechanical connection between the first mechanical connector and the second mechanical connector in response to the direction of rotational movement between the first connection part and the second connection part wherein the rotation being configured to move an upper surface of the asymmetrical plate structure, the upper surface facing the plane arrangement, against a surface of the flat structure of the second connection part.

6. The bio-signal apparatus of claim 4, wherein the flexible patch electrode comprises a first positional structure that is a counterpart for a second positional structure of the first mechanical connection part, the first positional structure and the second positional structure being configured to attach together in response to the rotation tightening the mechanical connection between the first mechanical connector and the second mechanical connector by the rotational movement between the first connection part and the second mechanical connector, the first positional structure and the second positional structure being configured to keep the flexible patch electrode and the bio-signal receiving device immobile with respect to each other.

7. The bio-signal receiving device of claim 1, wherein the asymmetrical plate structure comprises sectorial extensions of different radial lengths to restrict orientation during connection.

8. The bio-signal receiving device of claim 1, further comprising at least one positional structure configured to cooperate with a counterpart positional structure to maintain immobility during attachment.

9. The bio-signal receiving device of claim 1, wherein the first connection part comprises at least one locking pin configured to engage with a corresponding locking hole of a counterpart structure.

10. The bio-signal receiving device of claim 2, wherein the sectorial extensions are configured to allow insertion into an asymmetrical hole of a counterpart only in a predetermined orientation.

11. The bio-signal receiving device of claim 1, wherein the asymmetrical plate structure is configured to cooperate with a wedge structure of a counterpart to tighten the mechanical connection in response to rotation in one direction and loosen in response to rotation in an opposite direction.

12. The bio-signal receiving device of claim 3, wherein the wear-proof material is configured to withstand repeated rotational attachment and release.

* * * * *